(12) United States Patent
Clark

(10) Patent No.: US 8,777,982 B2
(45) Date of Patent: Jul. 15, 2014

(54) DEVICE FOR ACHIEVING HEMOSTASIS

(75) Inventor: Timothy W. I. Clark, Philadelphia, PA (US)

(73) Assignee: Forge Medical, Inc., Philadelphia, PA (US)

( * ) Notice: Subject to any disclaimer, the term of this patent is extended or adjusted under 35 U.S.C. 154(b) by 60 days.

(21) Appl. No.: 13/010,549

(22) Filed: Jan. 20, 2011

(65) Prior Publication Data

US 2011/0196417 A1    Aug. 11, 2011

Related U.S. Application Data

(63) Continuation-in-part of application No. 12/378,919, filed on Feb. 21, 2009, now abandoned.

(51) Int. Cl.
*A61B 17/00*        (2006.01)
*A61B 17/132*      (2006.01)

(52) U.S. Cl.
CPC ........... *A61B 17/0057* (2013.01); *A61B 17/132* (2013.01)
USPC ............................................ 606/201; 602/53

(58) Field of Classification Search
CPC ..................................................... A61B 17/00
USPC ...................... 606/200, 201; 601/134; 602/53
See application file for complete search history.

(56) References Cited

U.S. PATENT DOCUMENTS

| | | | |
|---|---|---|---|
| 3,086,530 A | 4/1963 | Groom | |
| 5,263,965 A | 11/1993 | Roth | |
| 5,728,120 A | 3/1998 | Shani et al. | |
| 6,068,646 A * | 5/2000 | Lam | 606/203 |
| 6,316,686 B1 | 11/2001 | Byrd | |
| 7,780,612 B2 | 8/2010 | Ross | |
| 2004/0068290 A1* | 4/2004 | Bates et al. | 606/202 |
| 2009/0171192 A1* | 7/2009 | Patrick et al. | 600/424 |
| 2009/0281565 A1* | 11/2009 | McNeese | 606/201 |
| 2010/0152770 A1 | 6/2010 | Spencer | |

FOREIGN PATENT DOCUMENTS

EP       0067622 A1    12/1982

OTHER PUBLICATIONS

International Search Report mailed May 23, 2012 for International Application No. PCT/US2012/022030.

\* cited by examiner

*Primary Examiner* — Darwin Erezo
*Assistant Examiner* — Diane Yabut
(74) *Attorney, Agent, or Firm* — Gordon & Rees LLP; Joshua R. Slavitt

(57) ABSTRACT

A device configured to apply a compressive force to a patient's skin at the site of a wound to assist in hemostasis. The device includes a footplate configured to adhere to the patient's skin, a receiving device positioned on the footplate, a plunger positioned within the receiving device and configured to move through both the receiving device and the footplate such that a downward force applied on the plunger toward the patient's skin results in the plunger moving through the receiving device and the footplate until the plunger contacts the patient's skin, and the plurality of motion restricting components interposed between the receiving device and the plunger, the plurality of motion restricting components configured such that as the plunger moves toward the skin movement of the plunger away from the skin is restricted until the restricting components are released.

15 Claims, 3 Drawing Sheets

DEVICE FOR ACHIEVING HEMOSTASIS

CROSS REFERENCE TO RELATED APPLICATIONS

This application is a continuation-in-part of U.S. patent application Ser. No. 12/378,919, now abandoned, filed Feb. 21, 2009, the content of which is hereby incorporated by reference in its entirety.
Not Applicable

BACKGROUND

The present disclosure relates to a device for achieving hemostasis at the site of a wound.

There are many devices and procedures currently employed in the medical field for achieving hemostasis at the site of a wound resulting, for example, from a dialysis procedure.

Among such prior art devices and procedures are, for example: a non-woven sponge manually applied directly to the site of the bleeding at the wound; clamp-type devices around the arm of the patient; and notch-shaped compression pad tightened around the arm of the patient much like an electrical tie.

Each of these prior art devices and procedures require extensive interaction with a patient by a medical technician. For example, a non-woven sponge requires the medical technician apply pressure to the wound until hemostasis is achieved. Similarly, a notch-shaped compression device requires the medical technician to use both hands to wrap the device around the arm (or leg) or a patient such that the pressure is applied appropriately to the wound. None of these prior art devices provides the medical technician with a device that can be applied with a single hand in a manner that allows the medical technician to leave the patient before hemostasis is achieved.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this document is to be construed as an admission that the embodiments described in this document are not entitled to antedate such disclosure by virtue of prior invention. As used in this document, the term "comprising" means "including, but not limited to."

In one general respect, the embodiments disclose a device configured to apply a compressive force to a patient's skin at the site of a wound to assist in hemostasis. The device comprises a footplate, a receiving device positioned on the footplate, a plunger positioned within the receiving device and configured to move therethrough, and motion restricting means interposed between the receiving device and the plunger, the motion restricting means configured such that as the plunger moves toward the skin movement of the plunger away from the skin is restricted until the restricting means are released.

In another general respect, the embodiments disclose a device configured to apply a compressive force against a patient's skin at the site of a wound to assist in hemostasis. The device comprises a footplate configured to adhere the device to the patient's skin, a receiving device positioned on the footplate, a plunger positioned within the receiving device and configured to move through both the receiving device and the footplate such that a downward force applied on the plunger toward the patient's skin results in the plunger moving through the receiving device and the footplate until the plunger contacts the patient's skin, and motion restricting means interposed between the receiving device and the plunger, the motion restricting means configured such that as the plunger moves toward the skin movement of the plunger away from the skin is restricted until the restricting means are released.

BRIEF DESCRIPTION OF THE DRAWINGS

Referring now to the drawings, in which like numerals represent like parts in the several views.

DETAILED DESCRIPTION

Figure 3:
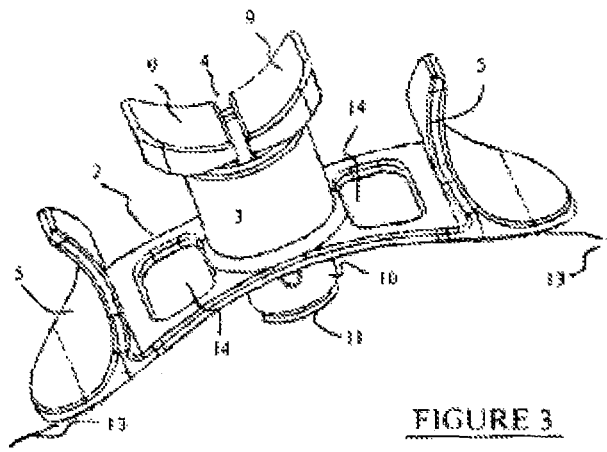
FIG. 3 illustrates the hemostasis device of FIG. 1, showing the plunger fully advanced in the cylinder against a wound site.

The present disclosure relates to a hemostasis device configured to apply pressure to a bleeding wound on a patient. The hemostasis device is configured such that a medical technician may adhere the device about the wound, apply pressure to the wound using a mechanical plunger, and leave the hemostasis device adhered to the patient until hemostasis is achieved. The hemostasis device may be sized and configured such that it may be used on a patient's forearm, upper arm, head, chest, back, thigh, lower leg, or any other body part. As discussed herein, the hemostasis device is applied to a puncture wound resulting from a hemodialysis procedure; however, the hemostasis device as discussed herein may be applied to any type of wound where hemostasis is desired. For example, the hemostasis device described herein may be applied to wounds resulting from abrasions, incisions, lacerations, avulsions, amputations, or any other wound where hemostasis is desired.

An exemplary hemostasis device 1 may comprise a footplate 2, a receiving device such as cylinder 3 positioned on the footplate 2, a plunger 4 and, in the embodiments of FIGS. 1-3 and 5, one or more stabilizing means such as the one or more curved arms 5 on the footplate 2. The footplate 2 may be made from a flexible material such that the contour of the footplate is capable of adjusting to various areas of the body having different curvatures. Also, it should be noted that the receiving device is shown as a cylinder 3 by way of example only.

Additional shapes such as a rectangle, square, oval, or other geometric shape that allows the receiving device to accept the plunger 4.

The engagement of the plunger 4 within the cylinder 3 provides for one-directional movement of the plunger 4 with respect to the cylinder 3 such as, for example, by use of a ratcheting mechanism. In one embodiment, one or more racks 6 positioned on the plunger 4 may engage a pawl 15 positioned in cylinder 3 in such manner as to limit plunger 4 to movement downwardly in cylinder 3. In other words, plunger 4 may be forced downwardly toward the wound site, but is restrained from upward movement in the cylinder 3 by the combination and position of the one or more racks 6 and the internally positioned pawl 15 resulting in a ratcheting in the cylinder 3. In another embodiment, one or more racks 6 on the cylinder 3 may engage a pawl positioned on plunger 4 in such manner as to limit plunger 4 to movement downwardly in cylinder 3. In yet another embodiment, one or more racks 6 on the plunger 4 may engage corresponding racks 16 positioned in cylinder 3 in such manner as to limit plunger 4 to movement downwardly in cylinder 3.

As shown in the embodiments represented in FIGS. 1-5, an upper portion of the plunger 4 may be bifurcated as indicated by the numerals 7 and 8 whereby, due to the resilience of the material from which the plunger 4 is made, to force the bifurcations 7 and 8 outwardly against the interior of the cylinder 3, thereby to force the external ratchets 6 on plunger 4 into engagement with the internal ratchets in cylinder 3. As discussed above, this arrangement restrains the plunger 4 from upward movement in the cylinder 3.

The bifurcated portions 7 and 8 at the top of the plunger 4 may be, at their extreme upper ends, arcuate shaped 9, and are adapted to be engaged by a medical technician when the hemostasis device 1 is operated. For example, the medical technician may engage the top of the plunger 4 with their finger, thumb, palm, or other body part that allows the medical technician to assert a downward pressure on the plunger.

The bottom of the plunger 4 may include a compression surface 10 having a compression pad 11 adhered thereto. The compression pad 11 may have a pro-coagulant coating such as calcium alginate, oxidized regenerated cellulose, seaweed extracts, a pro-coagulant polymer, another pro-coagulant coating, or combinations of two or more of these. The compression pad 11 may also have an antimicrobial coating such as silver or chlorhexidine.

One or more pads 12, with adhesive surfaces on both faces thereof, may be applied to the bottom of the footplate 2 such that, during operation, the pads may adhere to the skin 13 of the patient when the hemostasis device 1 is in use, thereby securing the footplate 2 to the patient's skin to prevent the hemostasis device from shifting position on the skin when in use. The size of the pads 12 may be determined relative to the pressure being applied by the hemostasis device 1 to the wound site and/or the part of the body to which the hemostasis device 1 is being applied. The size of the pads 12 may also be determined relative to the type of adhesive used on the pads 12. For example, the pulling force exerted on the patient's skin by the one or more pads 12 should be greater than the compressive force applied on the wound site by the plunger 4. Higher compressive forces applied on the wound site may be achieved by increasing the surface area of the pads 12 that are in contact with the skin, either by increasing the size and/or number of pads 12, using an adhesive having greater adhesive strength, or a combination of the two. Typical temporary medical adhesives may be used such that when hemostasis is achieved, the hemostasis device 1 is easily removed.

Figure 2:
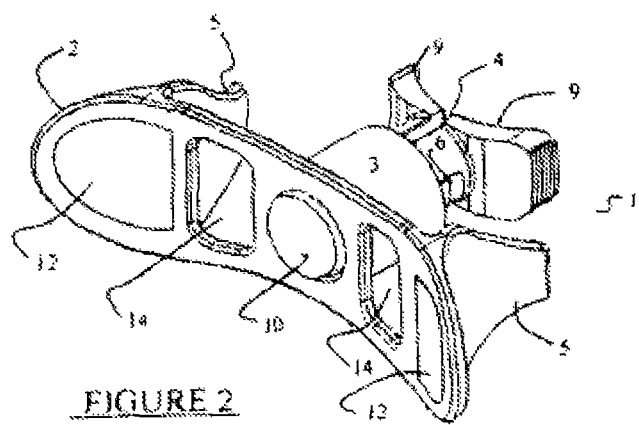
FIG. 2 illustrates the hemostasis device of FIG. 1 showing a plunger in an internally ratcheted cylinder prior to use.
Figure 1:
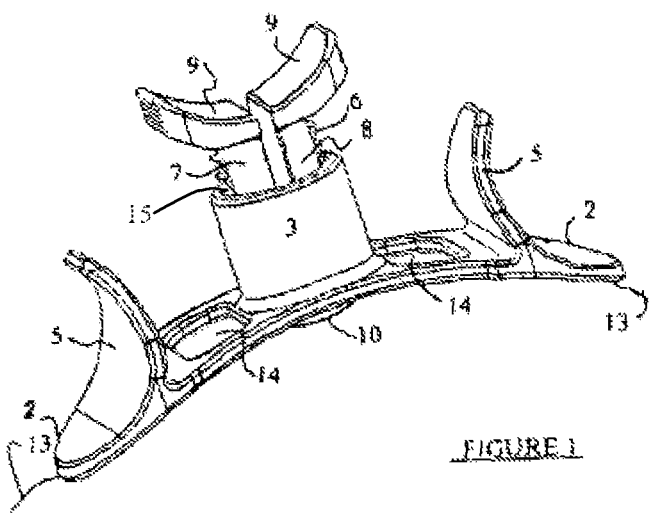
FIG. 1 illustrates an exemplary embodiment of a hemostasis device.

As shown in FIGS. 1-3, additional features such as curved arms 5 may be included on footplate 2. For example, the curved arms 5 may be engaged by the thumb and middle finger of the medical technician when the hemostasis device 1 is in use. Alternatively, the curved arms 5 may be engaged by the index and middle fingers of the medical technician when the hemostasis device 1 is in use. Either method of operation provides a single-handed operation style allowing the medical technician to quickly and efficiently apply the hemostasis device 1.

The footplate 2 may also be provided with apertures 14 configured and positioned to allow the medical technician to observe the position of the rounded portion 10 of the plunger 4 and the compression pad 11 relative to the site of the wound to assure that the hemostasis device 1 is properly positioned over the wound site.

It should be noted that the hemostasis device as shown in FIGS. 1-5 is shown by way of example only. Additional design features may be incorporated. For example, although only a ratcheting mechanism is disclosed herein to permit only unidirectional movement of plunger 4 in cylinder 3, additional locking mechanisms such as a screw machine (not shown herein) or other similar mechanisms may be employed. Similarly, the hemostasis device 1 may be formed by injection molding of a resilient thermoplastic polymer, although other equivalent materials and methods may be used.

The method of using the hemostasis device 1 to achieve hemostasis at the site of a puncture wound will now be described. In practice, after the removal of the needle from the puncture site in a patient's arm, the hemostasis device 1 may be positioned over the puncture site, the apertures 14 in the footplate 2 permitting visual observance by the medical technician to insure that the compression surface 10 of the plunger 4 and compression pad 11 adhered thereto are placed over the puncture site.

The adhesive pads 12 may securely hold the hemostasis device 1 in position on the skin 13. A finger of the medical technician may be placed on the arcuate elements 9 of the plunger 4. A second finger of the medical technician may be placed in engagement with one of the curved arms 5 as a third finger of the medical technician may be placed in engagement with the other of the curved arms 5. The first finger may be used to force down the plunger 4 until the compression pad 11 firmly bears against the puncture wound, the second and third fingers of the medical technician in clamping engagement with the curved arms 5 holding the hemostasis device 1 firmly in position until hemostasis is achieved. Because the plunger 4 is prevented from moving away from the puncture wound due to the ratcheting effect between the cylinder 3 and the plunger 4, the first finger of the medical technician may be removed from the arcuate elements 9 of the plunger 4. Similarly, as adhesive pads 12 may hold the hemostasis device to the skin 13 of the patient, the medical technician may remove their second and third fingers as well, leaving the device temporarily adhered to the patient's skin such that the plunger 4 maintains pressure on the puncture site.

After hemostasis has been achieved, the hemostasis device 1 may be removed from the skin 13 of the patient, and a surgical dressing may then be applied to the site of the puncture wound.

Figure 4:
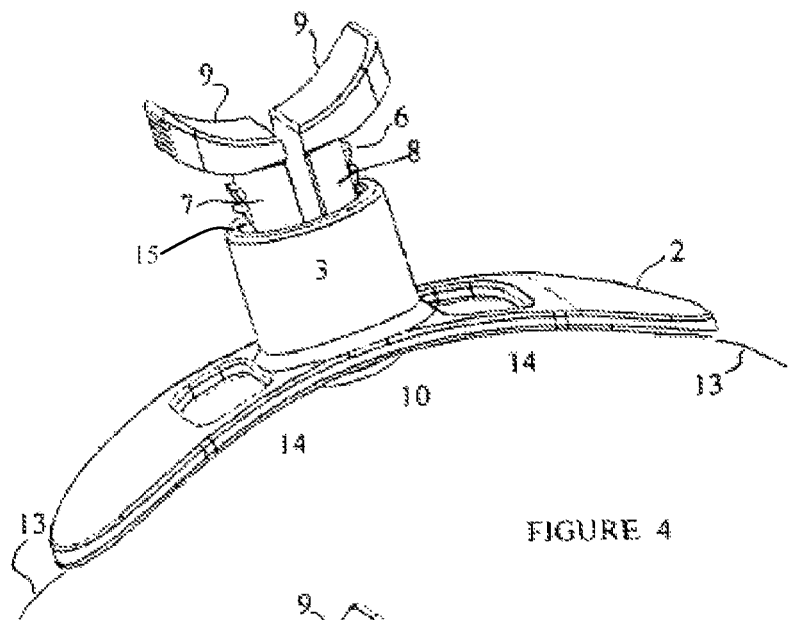
FIG. 4 illustrates a second exemplary embodiment of a hemostasis device.

In the alternate embodiment shown in FIG. 4, the curved arms 5 have been dispensed with. Two fingers, for example the thumb and middle finger of the medical technician, may engage the cylinder 3 on opposite sides thereof and function just as they did in the embodiment of FIGS. 1-3.

Figure 5:
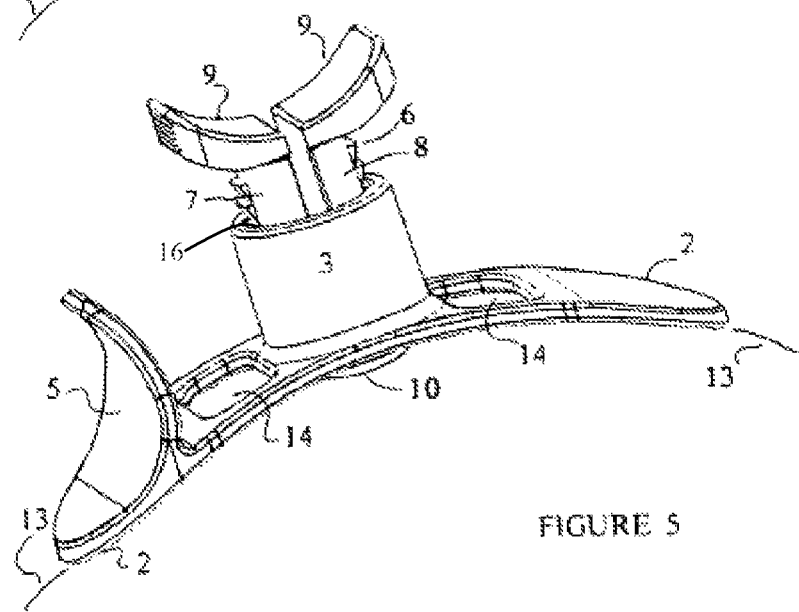
FIG. 5 illustrates a third exemplary embodiment of a hemostasis device.

In the alternate embodiment shown in FIG. 5, only one curved arm 5 is employed. Two fingers, for example the thumb and middle finger of the medical technician, may engage curved arm 5 and the side of cylinder 3 opposite the curved arm 5. In this embodiment, the thumb and middle finger of the medical technician function just as they did in the embodiment shown in FIGS. 1-3.

Figure 6:
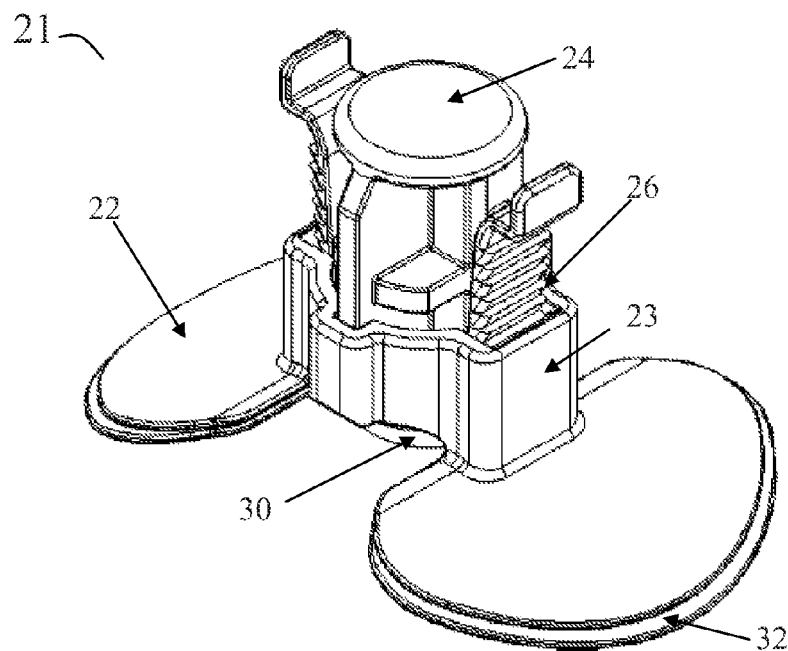
FIG. 6 illustrates a fourth exemplary embodiment of a hemostasis device.
Figure 7A:
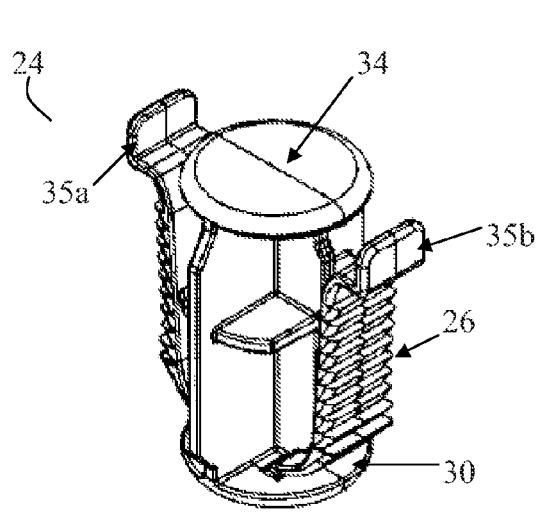
FIGS. 7A and 7B illustrate an exemplary plunger for use in the hemostasis device of FIG. 6.
Figure 7B:
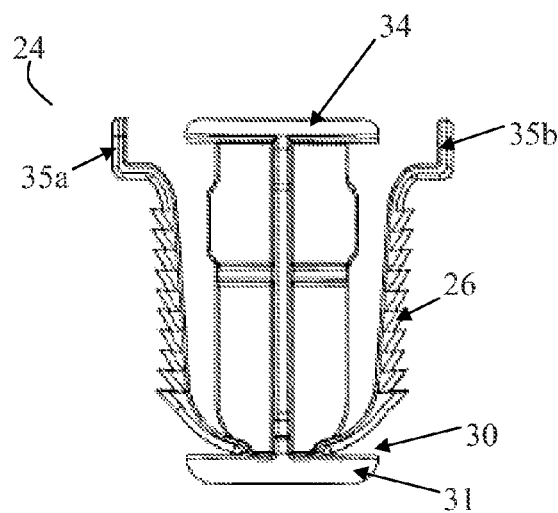

FIGS. 6, 7a and 7b illustrate another embodiment of the hemostasis device 21. Like hemostasis device 1, the hemostasis device 21 may comprise a footplate 22, a cylinder 23 centrally positioned on footplate 22, and a plunger 24. Though not shown in FIGS. 6, 7a and 7b, the footplate 22 may further include stabilizing means such as curved arms 5 as discussed above.

The engagement of the plunger 24 within the cylinder 23 provides for one-directional movement of the plunger 24 with respect to the cylinder 23 by use of a ratcheting mechanism. In the embodiment shown in FIGS. 6, 7a and 7b, a plurality of racks 26 attached to the plunger 24 may engage a corresponding pawl or rack (not shown) in the cylinder 23 in such manner as to limit the plunger 24 to movement downwardly in the cylinder 23. In other words, the plunger 24 may be forced downwardly toward the wound site, but is restrained from movement upwardly in the cylinder 23 by the combination and position of racks 26 and the corresponding pawls or racks in the cylinder 23. In another embodiment, a single rack 26 is attached to the plunger 24 and may engage a corresponding pawl or rack in the cylinder 23. In yet another embodiment, one or more racks 26 positioned on the cylinder 23 may engage a pawl positioned on plunger 24 in such manner as to limit plunger 24 to movement downwardly in cylinder 23.

As shown in FIGS. 7a and 7b, the plunger 24 may include various components. For example, the plunger 24 may be designed and configured such that the plunger includes a central plunger portion 34 and wings 35a and 35b. The central plunger portion 34 may be configured to receive applied downward force as provided by the medical technician. The wings 35a and 35b may include the racks 26 such that as the medical technician applies force to the central plunger portion 34, the wings 35a and 35b ratchet downward against the racks 26 of the cylinder 23. The wings 35a and 35b may also provide a means for releasing the pressure being applied to the wound by the plunger 24. The wings 35a and 35b may be squeezed toward the central plunger portion 34, thereby disengaging the racks 26, allowing the plunger 24 to move away from the wound site. This may be done when hemostasis is achieved or if too much pressure has been applied to the wound.

Similarly, the bottom of the plunger 24 may include a compression surface 30 having a compression pad 31 adhered thereto. The compression pad 31 may have a pro-coagulant coating such as calcium alginate, oxidized regenerated cellulose, seaweed extracts, a pro-coagulant polymer, another pro-coagulant coating, or combinations of two or more of these. The compression pad 31 may also have an antimicrobial coating such as silver or chlorhexidine.

One or more adhesive pads 32 having adhesive surfaces may be applied to the bottom of the footplate 22 such that, during operation, the pads 32 may adhere to the skin of the patient when the hemostasis device 21 is in use, thereby securing the footplate 22 to the patient's skin to prevent the hemostasis device from shifting position on the skin when in use. The size of the pads 32 may be determined relative to the pressure being applied by the hemostasis device 21 to the wound site and/or the part of the body to which the hemostasis device 1 is being applied. The size of the pads may also be determined relative to the type of adhesive being used on the pads. For example, the pulling force exerted on the patients skin by the one or more pads 32 should be greater than the compressive force applied on the wound site by the plunger 24. Higher compressive forces applied on the wound site may be achieved by increasing the surface area of the pads 12 that are in contact with the skin, either by increasing the size and/or number of pads 12, using an adhesive having greater adhesive strength, or a combination of the two. Typical temporary medical adhesives may be used such that when hemostasis is achieved, the hemostasis device 21 is easily removed.

The method as discussed above for operating hemostasis device 1 is applicable as well to hemostasis device 21. The hemostasis device 21 is placed on the skin of a patient about a wound and adhered to the skin via one or more adhesive pads 32. The plunger 24 is then pressed downward toward the wound site until appropriate pressure has been applied to the wound by the compression pad 31. The hemostasis device 21 is then left in position, thereby allowing the medical technician operating the device to perform other tasks until hemostasis is achieved.

It should be noted that the configurations and mechanisms discussed above are shown by way of example only. Additional configurations and mechanisms may be used to implement a hemostasis device. For example, a compressive force may be applied directly to the footplate. As above, the footplate may be adhered directly to a patient's skin proximal a wound. An inflatable bladder or other mechanical expander may be positioned between the footplate and the wound or between the footplate and a second plate positioned on the side of the footplate distal to the wound and attached to the footplate only at each end such that the bladder is positioned between the footplate and the second plate. The bladder or other mechanical expander may then be inflated, exerting a force against the footplate and thus providing a compressive force against the wound. Once hemostasis is achieved, the bladder or other mechanical expander may be deactivated and the footplate removed from the patient's skin. Examples of alternative mechanical expanders that may also be used include spring-loaded and threaded expanding devices.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A device configured for one-handed affixation to a patient's skin about a wound and application of a compressive force to the wound, the device comprising:
   a footplate comprising a bottom surface and one or more adhesive pads applied to the bottom surface and sized such that the adhesive strength of the one or more adhesive pads is greater than the compressive force applied to the wound, the footplate configured to be removably affixed to the patient's skin about the wound by one hand;
   a receiving device positioned on the footplate;
   a plunger positioned within the receiving device and configured to be engaged by a digit of the hand to move the plunger through the receiving device toward the wound to apply the compressive force to the wound; and
   a plurality of motion restricting components interposed between the receiving device and the plunger, wherein the plurality of motion restricting components comprise at least one first ratcheting component within the receiving device and at least one second ratcheting component on the plunger such that as the plunger moves through the receiving device said at least one second ratcheting component engages said at least one first ratcheting component, thereby restricting the plunger from moving away from the patient's skin.

2. The device of claim 1, wherein the footplate further comprises stabilizing means.

3. The device of claim 2, wherein the stabilizing means comprises at least one curved protrusion extending away from the footplate.

4. The device of claim 1, wherein said at least one second ratcheting component on the plunger is arranged on a plurality of wings positioned about a central plunger portion.

5. The device of claim 4, wherein the wings are configured such that moving the wings toward the central plunger portion disengages the at least one second ratcheting component on the plunger from the at least one first ratcheting component within the receiving device.

6. The device of claim 1, wherein the plurality of motion restricting components comprises a plurality of racks within the receiving device and a plurality of racks on the plunger such that as the plunger moves through the receiving device at least one rack on the plunger engages at least one rack within the receiving device, thereby restricting the plunger from moving away from the patient's skin.

7. The device of claim 1, wherein the plunger further comprises a compression pad for applying pressure to the patient's skin.

8. A device configured for one-handed affixation to a patient's skin about a wound and application of a compressive force to the wound, the device comprising:
  a footplate comprising a bottom surface and one or more adhesive pads applied to the bottom surface and sized such that the adhesive strength of the one or more adhesive pads is greater than the compressive force applied to the wound, the footplate configured to be removably affixed to the skin about the wound;
  a receiving device positioned on the footplate, the receiving device configured to be engaged by at least one digit of a user's hand for one-handed affixation to the skin about the wound;
  a plunger positioned within the receiving device and configured to be engaged by another digit of the user's hand for one-handed affixation to the skin about the wound and for moving the plunger through the receiving device toward the wound to apply the compressive force to the wound; and
  a plurality of motion restricting components interposed between the receiving device and the plunger, wherein the plurality of motion restricting components comprises at least one first ratcheting component within the receiving device and at least one second ratcheting component on the plunger such that as the plunger moves through the receiving device said at least one second ratcheting component engages said at least one first ratcheting component, thereby restricting the plunger from moving away from the patient's skin.

9. The device of claim 8, wherein the footplate further comprises stabilizing means.

10. The device of claim 9, wherein the stabilizing means comprises at least one curved protrusion extending away from the footplate.

11. The device of claim 8, wherein the at least one second ratcheting component on the plunger is arranged on a plurality of wings positioned about a central plunger portion.

12. The device of claim 11, wherein the wings are configured such that moving the wings toward the central plunger portion disengages the at least one second ratcheting component on the plunger from the at least one first ratcheting components within the receiving device.

13. The device of claim 8, wherein the plurality of motion restricting components comprises a plurality of racks within the receiving device and a plurality of racks on the plunger such that as the plunger moves through the receiving device at least one rack on the plunger engages at least one rack within the receiving device, thereby restricting the plunger from moving away from the patient's skin.

14. The device of claim 8, wherein the plunger further comprises a compression pad for applying pressure to the patient's skin.

15. A one-handed method of assisting in the hemostasis of a wound, the method comprising the steps of:
  adhesively anchoring a footplate to a patient's skin proximal to the wound with one hand, the footplate having a bottom surface, one or more adhesive pads applied to the bottom surface and sized such that the adhesive strength of the one or more adhesive pads is greater than the compressive force applied to the wound, and a receiving device positioned thereon, a plunger positioned within the receiving device and configured to move through the receiving device, and a plurality of motion restricting components interposed between the receiving device and the plunger;
  advancing the plunger through the receiving device toward the wound by the engagement of another digit of the user's hand until the plunger applies a compressive force to the wound; and
  engaging the plurality of motion restricting components to restrict reverse movement of the plunger through the receiving device, wherein the plurality of motion restricting components comprises a at least one first ratcheting component within the receiving device and at least one second ratcheting component on the plunger such that as the plunger moves through the receiving device said at least one second ratcheting component engages said at least one first ratcheting component, thereby restricting the plunger from moving away from the patient's skin.

* * * * *